(12) United States Patent
Woerner et al.

(10) Patent No.: US 12,358,937 B2
(45) Date of Patent: Jul. 15, 2025

(54) PRECIOUS METAL COMPOUNDS

(71) Applicant: Umicore AG & Co. KG, Hanau-Wolfgang (DE)

(72) Inventors: Eileen Woerner, Nidderau (DE); Timo Ebert, Kahl (DE); Michael Lennartz, Frankfurt (DE); Ralf Karch, Kleinostheim (DE); Angelino Doppiu, Seligenstadt (DE); Andreas Rivas-Nass, Bensheim (DE); Annika Frey, Hanau (DE)

(73) Assignee: Umicore AG & Co. KG, Hanau-Wolfgang (DE)

(*) Notice: Subject to any disclaimer, the term of this patent is extended or adjusted under 35 U.S.C. 154(b) by 507 days.

(21) Appl. No.: 17/745,949

(22) Filed: May 17, 2022

(65) Prior Publication Data

US 2022/0389042 A1    Dec. 8, 2022

Related U.S. Application Data

(62) Division of application No. 16/080,066, filed as application No. PCT/EP2017/054529 on Feb. 27, 2017, now Pat. No. 11,352,385.

(30) Foreign Application Priority Data

Feb. 26, 2016 (EP) ..................... 16157675

(51) Int. Cl.
| | | |
|---|---|---|
| *C07F 15/00* | (2006.01) | |
| *B01J 21/04* | (2006.01) | |
| *B01J 21/08* | (2006.01) | |
| *B01J 23/42* | (2006.01) | |
| *B01J 35/56* | (2024.01) | |
| *B01J 37/03* | (2006.01) | |
| *C07C 211/63* | (2006.01) | |

(52) U.S. Cl.
CPC ........... *C07F 15/0093* (2013.01); *B01J 23/42* (2013.01); *B01J 35/56* (2024.01); *B01J 37/035* (2013.01); *C07C 211/63* (2013.01); *C07F 15/0066* (2013.01); *C07F 15/008* (2013.01); *B01J 21/04* (2013.01); *B01J 21/08* (2013.01)

(58) Field of Classification Search
CPC .............. C07F 15/0093; C07F 15/0066; C07F 15/008; B01J 23/42; B01J 35/56; B01J 37/035; B01J 21/04; B01J 21/08; C07C 211/63

See application file for complete search history.

(56) References Cited

U.S. PATENT DOCUMENTS

| | | | |
|---|---|---|---|
| 5,652,191 A * | 7/1997 | Patterson | ............ B01J 31/2291 556/136 |
| 6,746,716 B2 | 6/2004 | Kiessling et al. | |
| 6,963,016 B1 | 11/2005 | Murthy et al. | |
| 2006/0188772 A1 | 8/2006 | Starz et al. | |
| 2008/0039536 A1 | 2/2008 | Fisher et al. | |
| 2010/0126154 A1 | 5/2010 | Klingmann et al. | |
| 2015/0321187 A1* | 11/2015 | Dias | .......... B01J 23/52 502/180 |
| 2017/0304805 A1* | 10/2017 | Xu | .......... B01J 23/48 |

FOREIGN PATENT DOCUMENTS

| | | |
|---|---|---|
| CN | 103864855 A | 6/2014 |
| CN | 103880889 A | 6/2014 |
| EP | 1175948 A2 | 1/2002 |
| EP | 1273344 A1 | 1/2003 |
| JP | 2005-314739 A | 11/2005 |
| JP | 2008-503332 A | 2/2008 |
| JP | 2010-521302 A | 6/2010 |
| KR | 10-2007-0024623 A | 3/2007 |
| WO | 2005/123255 A1 | 12/2005 |
| WO | 2008/113457 A1 | 9/2008 |
| WO | 2008/145386 A2 | 12/2008 |
| WO | 2008/151731 A1 | 12/2008 |
| WO | 2015/168327 A1 | 11/2015 |

OTHER PUBLICATIONS

Ikegami et al., "Methylated molybdoplatinate—its unexpected ability to absorb methanol" Chem. Commun., 46, 2010, 785-787, 3 pages (Year: 2010).*
Fortea-Perez et al., "Structural insight into the reaction mechanism of Pd-catalyzed nitrile hydration: Trapping the [Pd(H2O)4]2+ cation through a supramolecular complex", Inorganica Chimica Acta, vol. 443, 2016, pp. 267-273.
International Preliminary Report on Patentability received for PCT Patent Application No. PCT/EP2017/054529, mailed on Sep. 7, 2018, 21 pages. (10 pages of English Translation and 11 pages of Original Document).
International Search Report for PCT/EP2017/054529 mailed May 12, 2017.
Kulapina et al., "Interaction of rhodium(III) with cetylpyridinium cations in alkaline media", XP055816748, Database Caplus [Online], Jan. 1, 1984, 1 page.
Written Opinion of the International Searching Authority for PCT/EP2017/054529 mailed May 12, 2017.
Zhengzheng Yang et al: "Size-dependent CO and propylene oxidation activities of platinum nanoparticles on the monolithic Pt/TiO 2-YO x diesel oxidation catalyst under simulative diesel exhaust conditions", Catalysis Science & Technology, vol. 5, No. 4, 2015, pp. 2358-2365.

* cited by examiner

*Primary Examiner* — Anthony J Zimmer
*Assistant Examiner* — Abdul-Rahman Yusuf Waleed Smari
(74) *Attorney, Agent, or Firm* — Faegre Drinker Biddle & Reath LLP

(57) ABSTRACT

The invention relates to tetraalkylammonium-tetra- or hexa-hydroxometallates such as tetraethylammonium hexahydroxoplatinate, (N(alkyl)4)y[M(OH)x], a method for the production thereof, and the use thereof for producing catalysts.

11 Claims, 1 Drawing Sheet

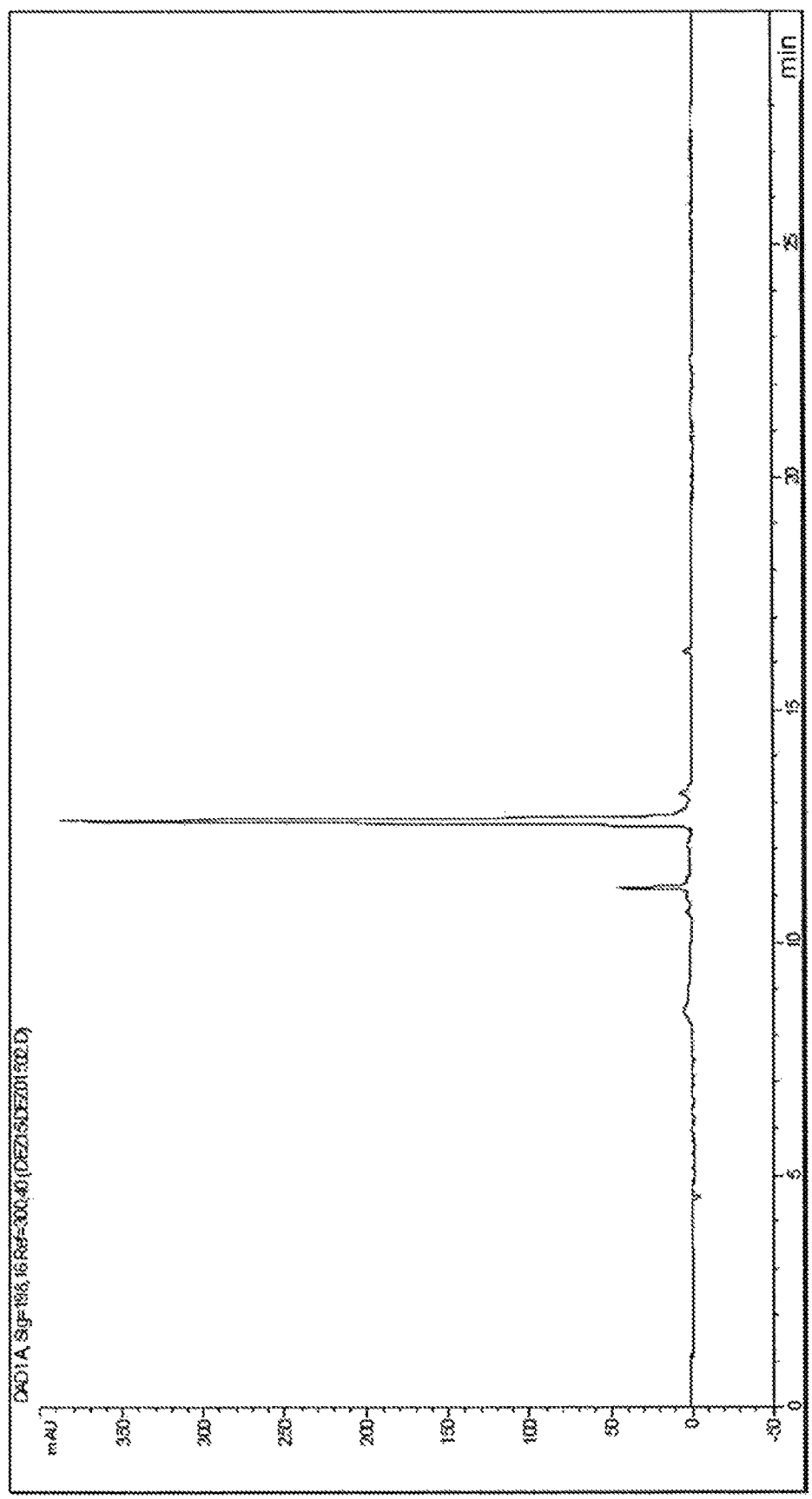

PRECIOUS METAL COMPOUNDS

CROSS-REFERENCE TO RELATED APPLICATIONS

This application is a division of U.S. Ser. No. 16/080,066, filed Aug. 27, 2018, which is a national stage application (under 35 U.S.C. § 371) of PCT/EP2017/054529, filed Feb. 27, 2017, which claims benefit of European Application No. 16157675.6, filed Feb. 26, 2016, all of which are incorporated herein by reference in their entirety.

During the deposition of platinum metal on substrate materials, e.g., oxide particles, several demands are placed on the platiniferous platinum starting compounds.

These shall advantageously be capable of production in basic solutions with a platinum content of approximately 10% (e.g., 9 to 11%), be halogen-free or at least halogen-poor, contain no foreign elements with the exception of carbon, hydrogen, oxygen, and nitrogen, and have the lowest possible nitrogen content in order to minimize nitrogen oxide emissions. In addition, they must be capable of precipitating as completely as possible by changing the pH value.

These conditions are met by tetraalkylammonium tetra- or hexa-hydroxy metallates of the formula $(N(alkyl)_4)_y[M(OH)_x]$, wherein
- M is a metal selected from the group consisting of rhodium, platinum, iridium, or palladium;
- alkyl is an alkyl group having up to 6 carbon atoms;
- Y is 1, 2, or 3; and
- X is 4 or 6.

Alkyl can, in particular, be an alkyl group selected from the group consisting of ethyl, propyl, isopropyl, n-butyl, isobutyl, tert-butyl, n-pentyl, sec-pentyl, 3-pentyl, 2-methylbutyl, isopentyl, 3-methylbutyl-2-yl, 2-methylbutyl-2-yl, neopentyl, n-hexyl, 3-methylpentyl, isohexyl, neohexyl, 2,3,-dimethylbutyl, or combinations thereof. The alkyl groups may be the same or different, but are, advantageously, the same.

In particular, tetraethylammonium hexahydroxy platinate $(N(CH_2CH_3)_4)_2[Pt(OH)_6]$—hereafter referred to as Pt-TEAH—has proved its worth. The compounds can be produced as a solution having the desired platinum concentration. The halogen content (especially, chlorine) is adjusted by means of the chlorine content of the reactants used.

These include, in particular, the following individual compounds of the general formula, $(N(alkyl)_4)_y[M(OH)_x]$, wherein alkyl, M, and x have the following meanings according to Formula 1:

| Number | M | X | Y | Alkyl |
|---|---|---|---|---|
| 1 | Rhodium | 6 | 3 | Ethyl |
| 2 | Rhodium | 6 | 3 | Propyl |
| 3 | Rhodium | 6 | 3 | Isopropyl |
| 4 | Rhodium | 6 | 3 | n-Butyl |
| 5 | Rhodium | 6 | 3 | Isobutyl |
| 6 | Rhodium | 6 | 3 | tert-Butyl |
| 7 | Rhodium | 6 | 3 | n-Pentyl |
| 8 | Rhodium | 6 | 3 | sec-Pentyl |
| 9 | Rhodium | 6 | 3 | 3-Pentyl |
| 10 | Rhodium | 6 | 3 | 2-Methylbutyl |
| 11 | Rhodium | 6 | 3 | Isopentyl |
| 12 | Rhodium | 6 | 3 | 3-Methylbut-2-yl |
| 13 | Rhodium | 6 | 3 | 2-Methylbut-2-yl |
| 14 | Rhodium | 6 | 3 | Neopentyl |
| 15 | Rhodium | 6 | 3 | n-Hexyl |
| 16 | Rhodium | 6 | 3 | 3-Methylpentyl |
| 17 | Rhodium | 6 | 3 | Isohexyl |
| 18 | Rhodium | 6 | 3 | Neohexyl |
| 19 | Rhodium | 6 | 3 | 2,3,-Dimethylbutyl |
| 20 | Platinum | 6 | 2 | Ethyl |
| 21 | Platinum | 6 | 2 | Propyl |
| 22 | Platinum | 6 | 2 | Isopropyl |
| 23 | Platinum | 6 | 2 | n-Butyl |
| 24 | Platinum | 6 | 2 | Isobutyl |
| 25 | Platinum | 6 | 2 | tert-Butyl |
| 26 | Platinum | 6 | 2 | n-Pentyl |
| 27 | Platinum | 6 | 2 | sec-Pentyl |
| 28 | Platinum | 6 | 2 | 3-Pentyl |
| 29 | Platinum | 6 | 2 | 2-Methylbutyl |
| 30 | Platinum | 6 | 2 | Isopentyl |
| 31 | Platinum | 6 | 2 | 3-Methylbut-2-yl |
| 32 | Platinum | 6 | 2 | 2-Methylbut-2-yl |
| 33 | Platinum | 6 | 2 | Neopentyl |
| 34 | Platinum | 6 | 2 | n-Hexyl |
| 35 | Platinum | 6 | 2 | 3-Methylpentyl |
| 36 | Platinum | 6 | 2 | Isohexyl |
| 37 | Platinum | 6 | 2 | Neohexyl |
| 38 | Platinum | 6 | 2 | 2,3,-Dimethylbutyl |
| 39 | Iridium | 6 | 2 or 3 | Ethyl |
| 40 | Iridium | 6 | 2 or 3 | Propyl |
| 41 | Iridium | 6 | 2 or 3 | Isopropyl |
| 42 | Iridium | 6 | 2 or 3 | n-Butyl |
| 43 | Iridium | 6 | 2 or 3 | Isobutyl |
| 44 | Iridium | 6 | 2 or 3 | tert-Butyl |
| 45 | Iridium | 6 | 2 or 3 | n-Pentyl |
| 46 | Iridium | 6 | 2 or 3 | sec-Pentyl |
| 47 | Iridium | 6 | 2 or 3 | 3-Pentyl |
| 48 | Iridium | 6 | 2 or 3 | 2-Methylbutyl |
| 49 | Iridium | 6 | 2 or 3 | Isopentyl |
| 50 | Iridium | 6 | 2 or 3 | 3-Methylbut-2-yl |
| 51 | Iridium | 6 | 2 or 3 | 2-Methylbut-2-yl |
| 52 | Iridium | 6 | 2 or 3 | Neopentyl |
| 53 | Iridium | 6 | 2 or 3 | n-Hexyl |
| 54 | Iridium | 6 | 2 or 3 | 3-Methylpentyl |
| 55 | Iridium | 6 | 2 or 3 | Isohexyl |
| 56 | Iridium | 6 | 2 or 3 | Neohexyl |
| 57 | Iridium | 6 | 2 or 3 | 2,3,-Dimethylbutyl |
| 58 | Palladium | 4 | 1 or 2 | Ethyl |
| 59 | Palladium | 4 | 1 or 2 | Propyl |
| 60 | Palladium | 4 | 1 or 2 | Isopropyl |
| 61 | Palladium | 4 | 1 or 2 | n-Butyl |
| 62 | Palladium | 4 | 1 or 2 | Isobutyl |
| 63 | Palladium | 4 | 1 or 2 | tert-Butyl |
| 64 | Palladium | 4 | 1 or 2 | n-Pentyl |
| 65 | Palladium | 4 | 1 or 2 | sec-Pentyl |
| 66 | Palladium | 4 | 1 or 2 | 3-Pentyl |
| 67 | Palladium | 4 | 1 or 2 | 2-Methylbutyl |
| 68 | Palladium | 4 | 1 or 2 | Isopentyl |
| 69 | Palladium | 4 | 1 or 2 | 3-Methylbut-2-yl |
| 70 | Palladium | 4 | 1 or 2 | 2-Methylbut-2-yl |
| 71 | Palladium | 4 | 1 or 2 | Neopentyl |
| 72 | Palladium | 4 | 1 or 2 | n-Hexyl |
| 73 | Palladium | 4 | 1 or 2 | 3-Methylpentyl |
| 74 | Palladium | 4 | 1 or 2 | Isohexyl |
| 75 | Palladium | 4 | 1 or 2 | Neohexyl |
| 76 | Palladium | 4 | 1 or 2 | 2,3,-Dimethylbutyl |

While the structure of hexahydroxy platinates is well-defined, the structure of other metal hydroxides is not always clearly characterized or even characterizable.

For example, in the case of rhodium, the compound according to the invention may thus have the structure, $[N(alkyl)_4]_3[Rh(OH)_6]$— for example, in the case of Rh-TEAH $[N(CH_2CH_3)_4]_3[Rh(OH)_6]$.

In the case of palladium, structures such as $(N(alkyl)_4)_2[Pd(OH)_4]$, but even $(N(alkyl)_4)[Pd(OH)_3(H_2O)]$, may also appear singly or in a mixture.

In general, the compounds may also exist in structures such as $(N(alkyl)_4)_s[M(OH)_v(H_2O)_w]^{u-v}$, in which u can be the charge of the metal, v=1 up to the coordination number of the metal, w=the coordination number of the metal −v, and s=1 up to u−v.

The described compounds, tetraalkylammonium tetra- or hexa-hydroxy metallates of the formula, $(N(alkyl)_4)_y[M(OH)_x]$, can be obtained through the reaction of hydroxy compounds of the metal, such as tetra- or hexa-hydroxy acids of the respective metals, with the respective tetraalkylammonium hydroxides—in a reaction medium, if necessary.

In the case of platinum, hexahydroxy platinic acid is particularly suitable as the hydroxy compound; with rhodium, rhodium hydroxide; with palladium, palladium hydroxide. These compounds can be precipitated by the addition of metal salts to a base, and thus obtained in this manner. Suitable bases include alkali metal hydroxides or their aqueous solutions, but also the tetraalkylammonium hydroxides that are used anyway, such as tetraethylammonium hydroxide in particular. An example of this is the precipitation of palladium hydroxide through the addition of a solution of palladium nitrate or palladium chloride to a solution of tetraethylammonium hydroxide. If a lowest-possible halogen content is desired, then the nitrate is, naturally, preferred over the halide.

These compounds cannot always be clearly characterized and may sometimes also have aquo-ligands. What is meant here is all such compounds, collectively with hydroxy compounds of a metal, such as their tetra- or hexa-hydroxy acids, as which the starting compounds may also be regarded. Thus, rhodium hydroxide is often described as $H_3[Rh(OH)_6]$.

For example, Pt-TEAH—tetraethylammonium hexahydroxy platinate—can be produced by the reaction of hexahydroxy platinic acid with tetraethylammonium hydroxide—optionally in the presence of a reaction medium.

The hydroxy compounds of a metal, such as tetra- or hexa-hydroxy acids of the respective metal, can be produced with varying halogen content—especially, chlorine content. Such halogen content is mostly 30,000 ppm or less, or 20,000 ppm or less, or 15,000 ppm or less—in particular, 10,000 ppm or less, 5,000 ppm or less, or 1,000 ppm or less—wherein the halogen content is in reference to the metal. Specifically, the halogen content is chlorine content, which can occur in the above-listed quantities.

Hexahydroxy platinic acid can be produced with varying halogen content—especially, chlorine content. These are, in general, 30,000 ppm or less, or 20,000 ppm or less, or 15,000 ppm or less—in particular, 10,000 ppm or less, 5,000 ppm or less, or 1,000 ppm or less—wherein the halogen content is in reference to the platinum metal.

It is not critical whether the hydroxy compounds of a metal, such as tetra- or hexa-hydroxy acids of the respective metal or the respective tetraalkylammonium hydroxide, are provided first and the respective reaction partner is added. Therefore, the hydroxy compounds of a metal such as tetra- or hexa-hydroxy acids of the desired metal or their solution can be provided, and a tetraalkylammonium hydroxide having the desired alkyl group—if necessary, in solution—be added, or the tetraalkylammonium hydroxide having the desired alkyl group or its solution can be provided, and the hydroxy compounds of the meal such as tetra- or hexa-hydroxy acids of the desired metal, if necessary in solution, be added.

In one embodiment, the addition of the reactants, hexahydroxy platinic acid and tetraethylammonium hydroxide, is not critical, which is why tetraethylammonium hydroxide or its solution can be provided and thereafter hexahydroxy platinic acid can be added, or hexahydroxy platinic acid can even first be provided and thereafter tetraethylammonium hydroxide or its solution can be added, and thereafter reacted with one another.

The reaction can optionally take place in a reaction medium, which can, advantageously, be a solvent. Polar, protic solvents are well suited.

The reaction medium can be selected from the group consisting of water, one or more alcohols, one or more acids, and mixtures thereof. In particular, the reaction medium can be selected from the group consisting of water, methanol, ethanol, propanol, isopropanol, butanol, 1-methylbutanol, 2-methylbutanol, tert-butanol, formic acid, acetic acid, propionic acid, and combinations thereof. Water is a particularly suitable reaction medium; in practice, demineralized water or distilled water are usually used in this case.

The reaction medium is, advantageously, provided prior to the addition of the reactants. It can, however, also be provided simultaneously with one reactant, e.g., if one reactant or both reactants are provided or added as a solution or suspension, such as, for example, a solution of tetraethylammonium hydroxide.

The reactants are reacted for a predetermined reaction time and at a reaction temperature lying within a predetermined range.

Generally, a reaction time of 10 minutes to 24 hours is sufficient—in particular, a reaction time of 20 minutes to 12 hours, 30 minutes to 6 hours, 45 minutes to 3 hours, or 45 minutes to 120 minutes, or 50 minutes to 70 minutes. A reaction time of approximately one hour is generally sufficient.

The reaction temperature can be from 10° C. to 100° C.—in particular, 15° C. to 80° C., or 20° C. to 50° C., or 20° C. to 40° C. If a reaction medium is used, then the maximum reaction temperature is the boiling point of the reaction medium. In practice, temperatures from 20° C. to 50° C. have proven useful.

To produce the desired tetraalkylammonium tetra- or hexa-hydroxy metallate of the formula $(N(alkyl)_4)_y[M(OH)_x]$, at least 0.5—in particular, at least 1.7—molar equivalents of tetraalkylammonium hydroxide per mole of the hydroxy compounds of the metal, such as tetra- or hexa-hydroxy acids of the metal, are used. 0.5 to 17 molar equivalents, 1.7 molar equivalents to 17 molar equivalents—in particular, 2 molar equivalents to 6 molar equivalents—of tetraalkylammonium hydroxide per mole of the hydroxy compounds of the metal, such as tetra- or hexa-hydroxy acids of the metal, have proven useful. If the metal M used is palladium, then, in particular, 0.5 to 2 molar equivalents—in particular, 1 to 1.7—molar equivalents of tetraalkylammonium hydroxide are advantageous.

In order to produce Pt-TEAH, for example, at least 1.7 molar equivalents of tetraethylammonium hydroxide per mole of hexahydroxy platinic acid are used. 1.7 molar equivalents to 17 molar equivalents—in particular, 2 molar equivalents to 6 molar equivalents—of tetraethylammonium hydroxide per mole of hexahydroxy platinic acid have proven useful.

If a reaction medium is used, the desired product (tetraalkylammonium tetra- or hexa-hydroxy metallate of the formula, $(N(alkyl)_4)_y[M(OH)_x]$, occurs as a solution—particularly, as an aqueous solution—in which the concentration of platinum, palladium, rhodium, or iridium is from 1 wt % to 15 wt %—in particular, 10 wt % to 15 wt %.

If the desired product is Pt-TEAH, then, if a reaction medium is used, it occurs as a solution—especially, an aqueous solution—in which the platinum concentration is from 1 wt % to 15 wt %—particularly, 10 wt % to 15 wt %.

The tetraalkylammonium tetra- or hexa-hydroxy metallates of the formula, $(N(alkyl)_4)_y[M(OH)_x]$, or their preparations can be used as precursor to the production of heterogeneous catalysts (such as automobile exhaust catalysts), for use in galvanic baths, as precursor product for the production of homogeneous catalysts, or even as a homogeneous catalyst itself. The foregoing are likewise suitable for the production of materials for fuel cells.

Pt-TEAH or its preparations, in particular, are well suited as precursors for the production of heterogeneous catalysts (e.g., automobile exhaust catalysts or fuel cells), for use in galvanic baths, as precursor product for the production of homogeneous catalysts, or even as a homogeneous catalyst itself.

To produce a heterogeneous catalyst, a solution of a tetraalkylammonium tetra- or hexa-hydroxy metallate of the formula, $(N(alkyl)_4)_y[M(OH)_x]$, can be mixed with a substrate such as a metal oxide—for example, aluminum oxide or silicon dioxide. The metal oxide, i.e., aluminum oxide or silicon dioxide, is used with advantage in the form of a powder or particles.

Thereafter, the tetraalkylammonium tetra- or hexa-hydroxy metallate of the formula, $(N(alkyl)_4)_y[M(OH)_x]$, is reacted, i.e., subjected to a chemical reaction, in which a metal compound develops—by precipitation, as the case may be—and is at least partially deposited on the surface of the substrate, i.e., the metal oxide particle. Therefore, the deposition can occur by precipitation, or even by adsorption.

Under certain favorable conditions, the elemental metal can also be deposited. For this to occur, a reducing agent must be added, such as hydrogen, hydrazine, or formic acid. This method is of particular interest for the production of materials for fuel cells.

The reaction and the precipitation of metal compounds can be accomplished by changing the pH value. In this instance, a hydroxy compound of the respective metal, in particular, such as the tetrahydroxy acid or hexahydroxy acid of the metal (i.e., rhodium, platinum, iridium, or palladium) can be precipitated and deposited on the metal oxide particles.

In a further process step, elemental metal can be produced on the particles of the substrate material through calcination of the metal oxide particles thus obtained on which the metal compounds have been deposited.

In one specific embodiment, for purposes of producing a heterogeneous catalyst, a solution of Pt-TEAH can be mixed with a substrate material such as a metal oxide, e.g., aluminum oxide or silicon dioxide, which is used with advantage in the form of a powder or particles.

Thereafter, the Pt-TEAH is reacted, i.e., subjected to a chemical reaction, in which a platinum compound is precipitated and is at least partially deposited on the surface of the particles of the substrate material, i.e., the metal oxide particles.

The reaction and the precipitation of the platinum compound can be accomplished by changing the pH value. In this instance, hexahydroxy platinic acid, in particular, can be precipitated and deposited on the metal oxide particles.

In a further process step, elemental platinum can be produced on the particles of the substrate material through calcination of the metal oxide particles thus obtained on which the metal compounds have been deposited.

Both the substrate material on which the metal compound—in particular, a platinum compound—was deposited, as well as substrate material on which the metal compound—in particular, a platinum compound converted into elemental metal through calcination—in particular, metallic platinum—can be used to produce automobile exhaust catalysts.

For this, a coating suspension (also referred to as a washcoat) is produced, which contains the substrate material. As described above, this generally comprises metal oxides—in particular, aluminum oxide or silicon dioxide.

By means of this coating suspension, the inner walls of the flow channels of the support bodies, which are necessary for the production of the automobile exhaust catalysts, are coated in a known manner, such as described in, for example, EP-A1-1273344.

The support bodies are usually manufactured from metal or ceramic and can be designed as flow-through honeycomb body or wall-flow filters. These are generally cylindrical bodies having a circumferential lateral surface and two oppositely arranged end faces, in which the support bodies are traversed by flow channels running between the two end faces.

Catalyst bodies with a round, elliptical, or triangular cross-section are widely used. In most cases, the flow channels have a square cross-section and are arranged in a tight pattern over the entire cross-section of the catalyst body. Depending upon the application case, the duct or cell density of the flow ducts in most cases varies between 10 and 250 $cm^{-2}$. Nowadays, catalyst support bodies with cell densities of around 62 $cm^{-2}$ are often still used for exhaust gas cleaning. In the case of wall-flow filters, these are alternatingly closed, so that a through-flowing exhaust gas stream is conducted via the pores to the walls that form the flow channels.

Following application of the coating suspension, the coated honeycomb bodies are subjected to additional process steps as necessary, dried, and, finally, calcinated. If the substrate material on which the platinum compound was deposited is used, then the transformation into elemental platinum takes place, during this calcination step, following coating of the support body.

If a substrate material that was calcinated following deposition of the platinum compound (e.g., platinum on an aluminum oxide substrate material) was already used to produce the coating suspension, then elemental platinum is already present on the substrate material prior to coating of the support body, and the calcination of the coated support body has no effect in terms of the transformation of the deposited platinum compound.

BRIEF DESCRIPTION OF THE DRAWINGS

FIG. 1 shows the result of product investigation using capillary electrophoresis.

EXAMPLES

Example 1: Production of Pt-TEAH
(Tetraethylammonium Hexahydroxy Platinate)

758 g of demineralized water in a reactor having a capacity of five liters was provided, and 1.47 kg of aqueous tetraethylammonium hydroxide solution at a concentration of 35 wt % was added, corresponding to approximately 2 moles per mole of platinum.

While stirring, 894.74 g of hexahydroxy platinic acid having a content of 38 g of platinum was then added. It was then stirred for one hour at a temperature of approximately 20° C. to 30° C., wherein a yellow-orange solution developed, which was filtered over a G4 glass frit and analyzed.

The solution had a precious metal content of 10.9 wt % platinum and a pH value of 13.9.

The product was also investigated using capillary electrophoresis, the result of which is shown in FIG. 1. The composition is characteristic of the compound, Pt-TEAH. The main peak corresponds to that of the $[Pt(OH)_6]^{2-}$ complex. The smaller, second peak corresponds to an additional anionic Pt complex of unknown composition, $[Pt(OH)_{6-x}(NEt)_x]^{2-x}$ (with x=1-2). The percentage distribution of the two main components can vary depending upon the production method and the quality of the reactants.

Example 2: Production of Rh-TEAH 13.5 g of rhodium hydroxide ($RhOH_3$) were suspended in 10 g of water, and 61.594 g of aqueous tetraethylammonium hydroxide solution at a concentration of 35 wt % was added in one shot and stirred for one hour at a temperature of 22° C., wherein a brown solution developed after approximately 30 minutes, which was filtered through a G4 glass frit and analyzed.

The solution had a precious metal content of 10 wt % and a pH value of approximately 10 (determined using universal indicator paper).

Example 3: Production of Pd-TEAH

Production of the Hydroxide 866 g of aqueous tetraethylammonium hydroxide solution at a concentration of 35 wt % were provided, and, over 30 minutes, approximately 540 g of a palladium nitrate solution with a palladium content of 130 g was dripped in until the pH value was 3.6 to 3.7; the exact amount of the solution depends upon the palladium content and can vary depending on that. During the addition, a heat of reaction occurred which resulted in a heating to 40° C.

It was stirred overnight for approximately 18 hours and filtered over a G4 glass frit. The solid obtained—the precipitated hydroxide—was washed with demineralized water until the filtrate took on a dark brown color, and was dried overnight in a vacuum.

Production of Pd-TEAH

Next, a 1.0 molar equivalent tetraethylammonium hydroxide solution with a concentration of 35 wt % was provided, and the dried filtrate was added and stirred for one hour at a temperature of 23° C. It was subsequently filtered over a G4 glass frit and dried.

The yield of $(N(alkyl)_4)_y[M(OH)_x]$ was 90%, relative to the palladium used.

The solution had a precious metal content of 10.2 wt % and a pH value of approximately 11 (determined with universal indicator paper).

Example 4: Production of Pt-TPAH
(Tetrapropylammonium Hexahydroxy Platinate;
Alkyl=n-Propyl)

The procedure was as in Example 1, although an aqueous solution of tetrapropylammonium hydroxide (40 wt %) was used, and an aqueous solution containing 31.92 wt % hexahydroxy platinic acid was provided and stirred for 180 minutes at 20° C. to 25° C., after which it was warmed to 50° C.; an additional 5 mL of the tetrapropylammonium hydroxide solution was added, left to stand overnight (approximately 18 hours), filtered over a G4 glass frit, and centrifuged for 15 minutes. The clear tetrapropylammonium hexahydroxy platinate solution thus obtained had a platinum content of 9.08%.

Example 5: Production of Pt-TBAH
(Tetrabutylammonium Hexahydroxy Platinate;
Alkyl=n-Butyl)

The procedure was as in Example 4, although a frozen tetrabutylammonium hydroxide*$30H_2O$ was used; an aqueous solution containing 39.3 wt % hexahydroxy platinic acid was provided and stirred overnight (approximately 18 hours) at 20° C. to 25° C., and centrifuged for 15 minutes. The clear tetrabutylammonium hexahydroxy platinate solution thus obtained displayed a dark yellow color.

The solution had a precious metal content of 9.8 wt % and a pH value of approximately 10 (determined with universal indicator paper).

Example 6: Production of a Coating Suspension for Production of a Heterogeneous Catalyst 45 g of aluminum oxide and 16 g of a zeolite (Zeolite-HSZ-0940NHA from Tosoh) were suspended in water and stirred for 15 minutes. Next, the pH value was adjusted to 10 through the addition of tetraethylammonium hydroxide, then 0.81 g of dissolved platinum in the form of a soluble platinum compound were added and stirred for 15 minutes. Next, 0.54 g of palladium in the form of palladium nitrate in water were added and again stirred for 15 minutes. Next, the pH value was adjusted to a value of 5 with acetic acid, followed by 5 minutes of stirring. Next, the precious metal content remaining in water was determined.

Comparative Example 6a: The platinum was added in the form of an ethanolamine-hexahydroxy platinate solution in water. It was determined that, after conclusion of the experiment, 10% of the original palladium concentration and 20% of the original palladium concentration were present in the solute. The rest of the precious metal had precipitated on the supports (aluminum oxide and zeolite) that were present.

Example 6b: The platinum was added in the form of an aqueous solution of tetraethylammonium hexahydroxy platinate (Pt-TEAH). Following conclusion of the experiment, it was determined that there was no longer any platinum in the solution, and only 0.8% of the original palladium concentration remained in solution. The rest of the precious metal had precipitated on the supports (aluminum oxide and zeolite) that were present.

The invention claimed is:
1. A method of preparing tetraalkylammonium tetra- or hexa-hydroxy metallate of the formula $(N(alkyl)_4)_y[M(OH)_x]$, wherein
M is a metal selected from the group consisting of rhodium, platinum, or palladium;
alkyl is an alkyl group selected from the group consisting of ethyl, propyl, isopropyl, n-butyl, isobutyl, tert-butyl, n-pentyl, sec-pentyl, 3-pentyl, 2-methylbutyl, isopentyl, 3-methylbut-2-yl, 2-methylbut-2-yl, neopentyl, n-hexyl, 3-methylpentyl, isohexyl, neohexyl, 2,3-dimethylbutyl, and combinations thereof;
Y is 2, or 3; and
X is 6; said method comprising reacting hydroxy compounds of a metal selected from the group consisting of rhodium, platinum, or palladium with tetraalkylammonium hydroxide—optionally in the presence of a reaction medium.

2. The method according to claim 1, wherein a tetraalkylammonium hydroxide or a solution thereof is provided, and hydroxy compounds of a metal are added and reacted for a predetermined reaction time and at a reaction temperature lying within a predetermined range.

3. The method according to claim 1, wherein hydroxy compounds of a metal are provided, and tetraalkylammonium hydroxide or a solution thereof is added and reacted for a predetermined reaction time and at a reaction temperature lying within a predetermined range.

4. The method according to claim 1, wherein the reaction medium is provided prior to the addition of the reactants.

5. The method according to claim 1, wherein the reaction medium is a polar, protic solvent.

6. The method according to claim 1, wherein the reaction medium is selected from the group consisting of water, one or more alcohols, one or more acids, and mixtures thereof.

7. The method according to claim 1, wherein the reaction medium is a solvent selected from the group consisting of water, methanol, ethanol, propanol, isopropanol, butanol, 1-methylbutanol, 2-methylbutanol, tert-butanol, formic acid, acetic acid, propionic acid, and combinations thereof.

8. The method according to claim 1, wherein the method is carried out at a temperature of 10° C. to 100° C.

9. The method according to claim 1, wherein 0.5 to 17 molar equivalents of tetraethylammonium hydroxide per mole of hydroxy compounds of the metal are used.

10. The method according to claim 1, wherein 2 to 6-molar equivalents of tetraethylammonium hydroxide per mole of hydroxy compounds of the metal are used.

11. The method according to claim 1, wherein the method is carried out at a temperature of 20° C. to 40° C.

* * * * *